United States Patent
Cooke et al.

(10) Patent No.: US 7,709,677 B2
(45) Date of Patent: May 4, 2010

(54) PROCESS OF PREPARING ARYLETHANOLDIAMINES

(75) Inventors: Jason William Beames Cooke, Stevenage (GB); Bobby Neal Glover, Durham, NC (US); Ronnie Maxwell Lawrence, Stevenage (GB); Matthew Jude Sharp, Durham, NC (US); Maria Fumiko Tymoschenko, Durham, NC (US)

(73) Assignee: GlaxoSmithKline LLC, Philadelphia, PA (US)

( * ) Notice: Subject to any disclaimer, the term of this patent is extended or adjusted under 35 U.S.C. 154(b) by 0 days.

(21) Appl. No.: 12/189,941

(22) Filed: Aug. 12, 2008

(65) Prior Publication Data

US 2008/0306278 A1  Dec. 11, 2008

Related U.S. Application Data

(62) Division of application No. 10/470,907, filed as application No. PCT/US01/49355 on Dec. 17, 2001, now Pat. No. 7,425,639.

(30) Foreign Application Priority Data

Jan. 31, 2001  (GB)  .................................. 0102407.4

(51) Int. Cl.
C07C 229/00 (2006.01)
C07C 211/00 (2006.01)
(52) U.S. Cl. ........................................ 560/19; 564/336
(58) Field of Classification Search .................. 560/19; 564/336
See application file for complete search history.

(56) References Cited

U.S. PATENT DOCUMENTS

| 4,478,849 A | 10/1984 | Ainsworth et al. |
| 4,772,631 A | 9/1988 | Holloway et al. |
| 5,135,932 A | 8/1992 | Hauel et al. |
| 5,232,946 A | 8/1993 | Hurnaus et al. |

FOREIGN PATENT DOCUMENTS

| DE | 200619 | 5/1983 |
| EP | 0103830 A2 | 3/1984 |
| EP | 0455006 A | 11/1991 |
| EP | 0516349 A2 | 12/1992 |
| EP | 0516350 A2 | 12/1992 |
| EP | 0543662 A | 5/1993 |
| EP | 0565317 A2 | 10/1993 |
| WO | 9006299 A1 | 6/1990 |
| WO | 9501170 | 1/1995 |
| WO | 9533724 | 12/1995 |
| WO | 9721666 A | 6/1997 |
| WO | 9803485 | 1/1998 |
| WO | 9965877 A | 12/1999 |
| WO | 02060885 A | 8/2002 |

OTHER PUBLICATIONS

K-H Magosch et al.; "Addition of Epoxides to Cyclic Amidines"; Liebigs Annalen der Chemie; 1970; vol. 742; pp. 128-134; Verlag Chemie GMBH; Weinheim, Germany.
Karl H Wuensch et al.; "Benzo-Condensed 7-Membered Ring Heterocyclic Compounds. III. Synthesis and Cyclization of N-Aryl-N'-aroylethylenediames"; Chemische Berichte; 1969; vol. 102, No. 11; pp. 3891-3902; Verlag Chemie GMBH; Weinheim, Germany.
Partridge et al.; "Cyclic Amidines. Part XXIV. Cyclisation of N-Allyl-N'-arylacetamidines to Imidazolines, Dihydroquinazolines, and Dihydrobenzodiazepines"; J. Chem. Soc. Perkin Transaction I; 1973; pp. 453-456.

*Primary Examiner*—Taylor Victor Oh
(74) *Attorney, Agent, or Firm*—Kathryn L. Coutler; Robert H. Brink

(57) ABSTRACT

An improved process for preparing arylethanoldiamines is described. Compounds of this type are known to be useful as agonists at atypical beta-adrenoceptors (also known as beta-3-adrenoceptors).

3 Claims, No Drawings

PROCESS OF PREPARING ARYLETHANOLDIAMINES

CROSS-REFERENCE TO RELATED APPLICATIONS

This application is a Divisional of U.S. patent application Ser. No. 10/470,907 filed Jul. 31, 2003, which was filed pursuant to 35 U.S.C. §371 as a U.S. National Phase Application of International Patent Application No. PCT/US01/49355 filed Dec. 17, 2001, which claims priority from GB Patent Application No. 0102407.4 filed Jan. 31, 2001 in the United Kingdom, all of which are incorporated herein in their entirety.

FIELD OF THE INVENTION

The present invention relates to a process for the preparation of arylethanoldiamine derivatives. Compounds of this type are known to be useful as agonists at atypical beta-adrenoceptors (also known as beta-3-adrenoceptors).

BACKGROUND OF THE INVENTION

Atypical beta-adrenoceptors are known to occur in adipose tissue and the gastrointestinal tract. Atypical beta-adrenoceptor agonists have been found to be particularly useful as thermogenic anti-obesity agents and as anti-diabetic agents. Compounds having atypical beta-adrenoceptor agonist activity have also been described as being useful in the treatment of hyperglycaemia, as animal growth promoters, as blood platelet aggregation inhibitors, as positive inotropic agents and as antiatherosclerotic agents, and as being useful in the treatment of glaucoma.

Compounds which are agonists at atypical beta-adrenoceptors are described, for example, in WO 97/21665, WO 97/21666, WO 98/43953, WO 99/65877, WO 95/33724, EP 0455006 and EP 0543662.

SUMMARY OF THE INVENTION

The present inventors have found an improved process for preparing arylethanoldiamine derivatives. The process of the present invention offers the advantage of achieving higher yields than previous processes: the process is shorter involving fewer steps, the reactions are more selective, e.g. the regioselectivity of epoxide opening is highly selective. The process of the present invention also offers an environmental advantage in that the quantities of toxic byproducts and solvents are reduced. The use of boron containing reagents is also no longer required.

Accordingly, in one aspect the present invention provides a process for the preparation of a compound of Formula (IA) or a pharmaceutically acceptable derivative thereof:

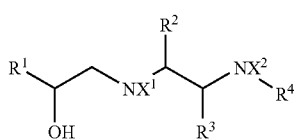

(IA)

wherein:

$R^1$ represents an aryl, phenoxymethyl or 5- or 6-membered heteroaromatic group, each of which is optionally substituted by one or more substituents selected from: halogen, $C_{1-6}$alkoxy, $C_{1-6}$alkyl, nitro, cyano, trifluoromethyl, —$NR^8R^9$ and —$NHSO_2R^8$;

$R^2$ represents hydrogen or $C_{1-6}$alkyl;

$R^3$ represents hydrogen or $C_{1-6}$alkyl;

$X^1$ and $X^2$ independently represent (a) hydrogen, (b) $C_{1-6}$alkylCO, or (c) an aryl CO group optionally substituted by halogen or a $C_{1-6}$alkyl group, with the proviso that when one is (b) or (c) the other is hydrogen (a);

$R^4$ represents (a) phenyl substituted by one or more groups selected from: $C_{1-6}$alkyl, halogen, trifluoromethyl, $C_{1-6}$alkoxy, —$CO_2H$ and —$CO_2R^8$, or (b) phenoxymethyl or a 5- or 6-membered heteroaromatic group, optionally substituted by one or more groups selected from: $C_{1-6}$alkyl, halogen, trifluoromethyl, $C_{1-6}$alkoxy, —$CO_2H$, —$CO_2R^8$, CN, $NO_2$, hydroxymethyl and —$CONHR^8$, or (c) a group (W):

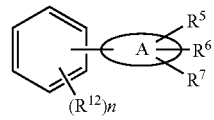

(W)

wherein A represents an aryl or 5- or 6-membered heteroaromatic group; $R^5$ represents cyano, tetrazol-5-yl, —$CO_2H$ or —$CO_2R^8$; $R^6$ and $R^7$ independently represent hydrogen, $C_{1-6}$alkyl, —$CO_2H$, —$CO_2R^8$, cyano, tetrazol-5-yl, halogen, trifluoromethyl or $C_{1-6}$alkoxy, or when $R^6$ and $R^7$ are bonded to adjacent carbon atoms, $R^6$ and $R^7$ may, together with the carbon atoms to which they are bonded, form a fused 5- or 6-membered ring optionally containing one or two nitrogen, oxygen or sulfur atoms; each $R^{12}$ independently represents substituents selected from: $C_{1-6}$alkyl, halogen, trifluoromethyl and $C_{1-6}$alkoxy, and n represents an integer from 0-4; and $R^8$ and $R^9$ independently represent $C_{1-6}$alkyl;

comprising the step of preparing a compound of Formula (IB) or a pharmaceutically acceptable derivative thereof:

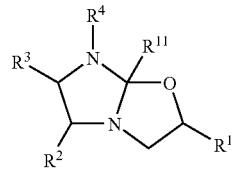

(IB)

wherein:

$R^1$ represents an aryl, phenoxymethyl or 5- or 6-membered heteroaromatic group, each of which is optionally substituted by one or more substituents selected from: halogen, $C_{1-6}$alkoxy, $C_{1-6}$alkyl, nitro, cyano, trifluoromethyl, —$NR^8R^9$ and —$NHSO_2R^8$;

$R^2$ represents hydrogen or $C_{1-6}$alkyl;

$R^3$ represents hydrogen or $C_{1-6}$alkyl;

$R^4$ represents (a) phenyl substituted by one or more groups selected from: $C_{1-6}$alkyl, halogen, trifluoromethyl, $C_{1-6}$alkoxy and —$CO_2R^8$, or (b) phenoxymethyl or a 5- or 6-membered heteroaromatic group, optionally substituted by one or more groups selected from: $C_{1-6}$alkyl, halogen, trifluoromethyl, $C_{1-6}$alkoxy, —$CO_2R^8$, CN, $NO_2$, hydroxymethyl and —$CONHR^8$, or (c) a group (W):

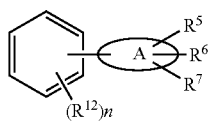

wherein A represents an aryl or 5- or 6-membered heteroaromatic group; $R^5$ represents cyano, tetrazol-5-yl or $—CO_2R^8$; $R^6$ and $R^7$ independently represent hydrogen, $C_{1-6}$alkyl, $—CO_2R^8$, cyano, tetrazol-5-yl, halogen, trifluoromethyl or $C_{1-6}$alkoxy, or when $R^6$ and $R^7$ are bonded to adjacent carbon atoms, $R^6$ and $R^7$ may, together with the carbon atoms to which they are bonded, form a fused 5- or 6-membered ring optionally containing one or two nitrogen, oxygen or sulfur atoms; each $R^{12}$ independently represents substituents selected from: $C_{1-6}$alkyl, halogen, trifluoromethyl and $C_{1-6}$alkoxy, and n represents an integer from 0-4;

$R^8$ and $R^9$ independently represent $C_{1-6}$alkyl; and $R^{11}$ represents $C_{1-6}$alkyl or aryl optionally substituted by $C_{1-6}$alkyl or halogen.

In an alternative aspect, the invention provides a process for the preparation of a compound of Formula (IA) or a pharmaceutically acceptable derivative thereof

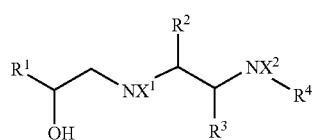

wherein:

$R^1$ represents an aryl, phenoxymethyl or 5- or 6-membered heteroaromatic group, each of which is optionally substituted by one or more substituents selected from: halogen, $C_{1-6}$alkoxy, $C_{1-6}$alkyl, nitro, cyano, trifluoromethyl, $—NR^8R^9$ and $—NHSO_2R^8$;

$R^2$ represents hydrogen or $C_{1-6}$alkyl;

$R^3$ represents hydrogen or $C_{1-6}$alkyl;

$X^1$ and $X^2$ independently represent (a) hydrogen, (b) $C_{1-6}$alkylCO, or (c) an aryl CO group optionally substituted by halogen or a $C_{1-6}$alkyl group, with the proviso that when one is (b) or (c) the other is hydrogen (a);

$R^4$ represents (a) phenyl substituted by one or more groups selected from: $C_{1-6}$alkyl, halogen, trifluoromethyl, $C_{1-6}$alkoxy, $—CO_2H$ and $—CO_2R^8$, or (b) phenoxymethyl or a 5- or 6-membered heteroaromatic group, optionally substituted by one or more groups selected from: $C_{1-6}$alkyl, halogen, trifluoromethyl, $C_{1-6}$alkoxy, $—CO_2H$, $—CO_2R^8$, nitro, CN, $NO_2$, hydroxymethyl and $—CONHR^8$, or (c) a group (W):

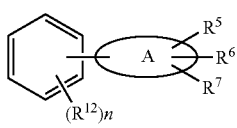

wherein A represents an aryl or 5- or 6-membered heteroaromatic group; $R^5$ represents cyano, tetrazol-5-yl, $—CO_2H$ or $—CO_2R^8$; $R^6$ and $R^7$ independently represent hydrogen, $C_{1-6}$alkyl, $—CO_2H$, $—CO_2R^8$, cyano, tetrazol-5-yl, halogen, trifluoromethyl or $C_{1-6}$alkoxy, or when $R^6$ and $R^7$ are bonded to adjacent carbon atoms, $R^6$ and $R^7$ may, together with the carbon atoms to which they are bonded, form a fused 5- or 6-membered ring optionally containing one or two nitrogen, oxygen or sulfur atoms; each $R^{12}$ independently represents substituents selected from: $C_{1-6}$alkyl, halogen, trifluoromethyl and $C_{1-6}$alkoxy, and n represents an integer from 0-4; and $R^8$ and $R^9$ independently represent $C_{1-6}$alkyl;

comprising hydrolysis of a compound of Formula (IB) or a pharmaceutically acceptable salt thereof:

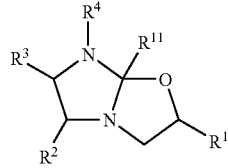

wherein:

$R^1$ represents an aryl, phenoxymethyl or 5- or 6-membered heteroaromatic group, each of which is optionally substituted by one or more substituents selected from: halogen, $C_{1-6}$alkoxy, $C_{1-6}$alkyl, nitro, cyano, trifluoromethyl, $—NR^8R^9$ and $—NHSO_2R^8$;

$R^2$ represents hydrogen or $C_{1-6}$alkyl;

$R^3$ represents hydrogen or $C_{1-6}$alkyl;

$R^4$ represents (a) phenyl substituted by one or more groups selected from: $C_{1-6}$alkyl, halogen, trifluoromethyl, $C_{1-6}$alkoxy and $—CO_2R^8$, or (b) phenoxymethyl or a 5- or 6-membered heteroaromatic group, optionally substituted by one or more groups selected from: $C_{1-6}$alkyl, halogen, trifluoromethyl, $C_{1-6}$alkoxy, $—CO_2R^8$, CN, $NO_2$, hydroxymethyl and $—CONHR^8$, or (c) a group (W):

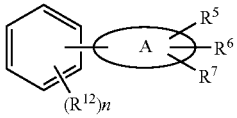

wherein A represents an aryl or 5- or 6-membered heteroaromatic group; $R^5$ represents cyano, tetrazol-5-yl or $—CO_2R^8$; $R^6$ and $R^7$ independently represent hydrogen, $C_{1-6}$alkyl, $—CO_2R^8$, cyano, tetrazol-5-yl, halogen, trifluoromethyl or $C_{1-6}$alkoxy, or when $R^6$ and $R^7$ are bonded to adjacent carbon atoms, $R^6$ and $R^7$ may, together with the carbon atoms to which they are bonded, form a fused 5- or 6-membered ring optionally containing one or two nitrogen, oxygen or sulfur atoms; each $R^{12}$ independently represents substituents selected from: $C_{1-6}$alkyl, halogen, trifluoromethyl and $C_{1-6}$alkoxy, and n represents an integer from 0-4;

$R^8$ and $R^9$ independently represent $C_{1-6}$alkyl; and $R^{11}$ represents $C_{1-6}$alkyl or aryl optionally substituted by $C_{1-6}$alkyl or halogen; and optionally when the group $R^4$ in formula IB is substituted by $—CO_2R^8$, the step of hydrolysing the ester group $—CO_2R^8$ to produce a compound of Formula (IA), wherein $R^4$ is substituted by a $—CO_2H$ group.

DETAILED DESCRIPTION OF THE INVENTION

As used herein, the terms "alkyl" and "alkoxy" mean both straight and branched chain saturated hydrocarbon groups. Examples of alkyl groups include methyl, ethyl, propyl and butyl groups. Examples of alkoxy groups include methoxy and ethoxy groups.

As used herein, the term "aryl" refers to an optionally substituted aromatic group with at least one ring having a conjugated pi-electron system, containing up to two conjugated or fused ring systems. "Aryl" includes monocyclic or bicyclic aromatic carbocyclic groups, such as phenyl and naphthyl, all of which may be optionally substituted. Preferred "aryl" moieties are unsubstituted, monosubstituted, disubstituted or trisubstituted phenyl and naphthyl. Preferred "aryl" substituents are selected from the group consisting of halogen, $C_{1-6}$alkoxy, $C_{1-6}$alkyl, nitro, cyano, trifluoromethyl, —$NR^8R^9$, —$NHSO_2R^8$ and —$CO_2R^8$.

As used herein, the term "heteroaromatic group" means an optionally substituted aromatic group containing one or more heteroatoms selected from: nitrogen, sulphur and oxygen atoms, with at least one ring having a conjugated pi-electron system, containing up to two conjugated or fused ring systems. Examples of 5-membered groups include unsubstituted, monosubstituted, disubstituted or trisubstituted thiophene, thiazole, pyrrole, pyrazole, imidazole and furan. Examples of 6-membered groups include unsubstituted, monosubstituted, disubstituted or trisubstituted pyridyl, pyrazyl and pyrimidyl. Preferred "heteroaromatic" substituents are selected from the group consisting of halogen, $C_{1-6}$alkoxy, $C_{1-6}$alkyl, nitro, cyano, trifluoromethyl, —$NR^8R^9$, —$NHSO_2R^8$, —$CO_2R^8$, CN, $NO_2$, hydroxymethyl and —$CONHR^8$.

As used herein, the term "halogen" means an atom selected from fluorine, chlorine, bromine and iodine.

Preferably, $R^1$ represents an aryl group optionally substituted by one or more substituents selected from: halogen, $C_{1-6}$alkoxy, $C_{1-6}$alkyl and trifluoromethyl. More preferably, $R^1$ represents phenyl substituted by a halogen group, which atom or group is preferably located in the meta position. Most preferably, $R^1$ represents phenyl substituted by a chlorine atom located in the meta position.

Preferably, $R^2$ represents hydrogen.

Preferably, $R^3$ represents hydrogen.

Preferably, $X^1$ and $X^2$ both represent hydrogen.

Preferably, $R^4$ represents group (W).

Preferably, A represents a phenyl or 5- or 6-membered heteroaromatic group. More preferably A represents a phenyl, pyridine, furan or thiophene group. Preferably A is located meta to the phenyl ring.

In a compound of Formula (IA), $R^5$ is preferably —$CO_2H$. In a compound of Formula (IB), $R^5$ is preferably —$CO_2CH_3$.

Preferably, $R^6$ and $R^7$ represent hydrogen.

Preferably, $R^{11}$ represents methyl.

Preferably, n represents 0.

It is to be understood that the present invention covers all combinations of suitable, convenient and preferred groups described herein above. Particularly preferred compounds, or compounds of the processes, of the invention include those in which each variable is selected from the preferred groups for each variable. Even more preferable compounds of the invention, or compounds of the processes, include those where each variable is selected from the more preferred or most preferred groups for each variable.

It will be appreciated that the above compounds of Formula (IA) are optically active. Processes for preparing individual, isolated isomers and mixtures thereof, including racemates, are within the scope of the present invention.

Preferably the compound of Formula (IA) is selected from:

3'-[(2-{[(2R)-2-(3-chlorophenyl)-2-hydroxyethyl] amino}ethyl)amino][1,1'-biphenyl]-3-carboxylic acid hydrochloride, 2-{3-[(2-{[(2R)-2-(3-chlorophenyl)-2-hydroxyethyl] amino}ethyl)amino]phenyl}-3-furoic acid, 3-{3-[(2-{[(2R)-2-(3-chlorophenyl)-2-hydroxyethyl] amino}ethyl)amino]phenyl}isonicotinic acid, 3'-[((2R)-2-{[(2R)-2-(3-chlorophenyl)-2-hydroxyethyl] amino}propyl)amino]-1,1'-biphenyl-2-carboxylic acid, and 2-{3-[(2-{[(2R)-2-(3-chlorophenyl)-2-hydroxyethyl] amino}ethyl)amino]phenyl}thiophene-3-carboxylic acid and pharmaceutically acceptable salts thereof.

Arylethanoldiamine derivatives are known to be beta-3-adrenoceptor agonists. Preferably the compound of Formula (IA) is a beta-3-adrenoceptor agonist. More preferably, the compound of Formula (IA) is a selective beta-3-adrenoceptor agonist.

As used herein, a "pharmaceutically acceptable derivative" means a pharmaceutically acceptable salt, ester, or salt of such ester, or any other compound which, upon administration to the recipient, is capable of providing (directly or indirectly) a compound of Formula (IA) or an active metabolite or residue thereof. It will be appreciated by those skilled in the art that the compounds of Formula (IA) may be modified to provide pharmaceutically acceptable derivatives thereof at any of the functional groups in the compounds of Formula (IA). Of particular interest as such derivatives are compounds modified at the carboxyl function, hydroxyl functions or at amino groups. It will be appreciated by those skilled in the art that the pharmaceutically acceptable derivatives of the compounds of Formula (IA) may be derivatised at more than one position.

Preferred pharmaceutically acceptable derivatives of the compounds of Formula (IA) are pharmaceutically acceptable salts thereof. Pharmaceutically acceptable salts of the compounds of Formula (IA) include those derived from pharmaceutically acceptable inorganic and organic acids and bases. Examples of suitable acids include hydrochloric, hydrobromic, sulphuric, nitric, perchloric, fumaric, maleic, phosphoric, glycollic, lactic, salicylic, succinic, toluene-p-sulphonic, tartaric, acetic, citric, methanesulphonic, formic, benzoic, malonic, naphthalene-2-sulphonic and benzenesulphonic acids. Other acids such as oxalic, while not in themselves pharmaceutically acceptable may be useful in the preparation of salts useful as intermediates in obtaining compounds of the invention and their pharmaceutically acceptable acid addition salts. Salts derived from appropriate bases include alkali metal (e.g. sodium), alkaline earth metal (e.g. magnesium), ammonium and $NR_4^+$ (where R is $C_{1-4}$alkyl) salts.

Preferably, hydrolysis of a compound of Formula (IB) to form a compound of Formula (IA) is carried out by reflux in the presence of an aqueous solution of a group 1 or group 2 metal hydroxide, e.g. NaOH or KOH, and preferably an alkanol, e.g. MeOH, for at least 4 hours. The hydrolysis may be full or partial. A compound of Formula (IA) in which $X^1$ or $X^2$ is (b) $C_{1-6}$alkylCO, or (c) an aryl CO group optionally substituted by halogen or a $C_{1-6}$alkyl group, can be produced by the partial hydrolysis of a compound of Formula (IB) and isolated by standard chromatography techniques.

The optional step of hydrolysing the ester group $-CO_2R^8$ to produce a compound of Formula (IA), wherein $R^4$ is substituted by a $-CO_2H$ group can be carried out by a further hydrolysis step under standard hydrolysis conditions as would be apparent to a skilled person.

In the following description, the groups $R^1$, $R^2$, $R^3$, $R^5$, $R^6$, $R^7$, $R^8$, $R^9$, $R^{11}$, $R^{12}$, W and A are as defined above unless otherwise stated. $R^4$ is as defined in Formula (IB) above unless otherwise stated.

A compound of Formula (IB) may be prepared by reacting a compound of Formula (II) with a compound of Formula (III):

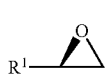
(II)

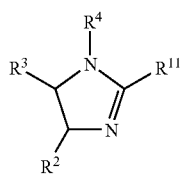
(III)

at elevated temperature and pressure, optionally in the presence of one or more of: $C_{3-6}$ alkanols, acetonitrile, N-methyl-pyrrolidinone (NMP), isobutylacetate, isopropylacetate, dimethylformamide (DMF), toluene, xylene or dimethylacetamide (DMA); preferably toluene and/or xylene. The temperature for the reaction is suitably 100° C. or greater, preferably 100-150° C., more preferably 100-120° C.

The reaction of a compound of Formula (II) with a compound of Formula (III) to form a compound of Formula (IB) and the subsequent conversion of a compound of Formula (IB) to a compound of Formula (IA) may be carried out separately or in situ. The reaction is preferably carried out in situ.

A compound of Formula (III) may be prepared from a compound of Formula (IV):

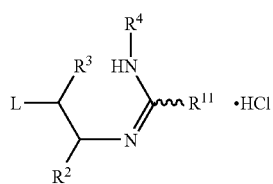
(IV)

wherein L represents a leaving group such as a halogen atom (e.g. chlorine), by cyclisation in the presence of a solvent selected from: dichloromethane (DCM), EtOAc, toluene and/or xylene, and a base selected from: $Na_2CO_3$, NaOH, anhydrous $Et_3N$ and/or an amine, e.g. aqueous $NH_3$. Preferably the solvent is DCM. Preferably the base is aqueous $NH_3$.

Compounds of Formula (IV) may be prepared from compounds of Formula (V)

(V)

using any suitable method for the preparation of amidines. For example, by condensation of a compound of Formula (VI) wherein L represents a leaving group as previously defined, in the presence of a solvent selected from: DCM, toluene, EtOAc or $CH_3CN$, and $PCl_5$ or $POCl_3$. Preferably the solvent is EtOAc. Preferably $PCl_5$ is present.

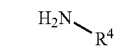
(VI)

Compounds of Formula (V) may be prepared by reaction of a compound of Formula (VII) with a compound of Formula (VIII) according to the method of Thompson, (*J. Org. Chem.* 1984, 49, 5237),

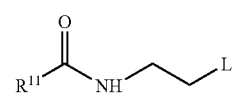
(VII)

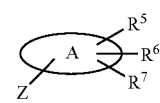
(VIII)

where Z is halogen or triflate, using a suitable boronic acid coupling conditions, e.g. palladium on carbon and sodium carbonate or $Pd(PPh_3)_4$ (tetrakis(triphenylphosphine)palladium (0)), followed by reduction of the nitro group using standard methods, e.g. under hydrogen using a suitable catalyst, such as palladium on carbon in a suitable solvent such as an alcohol, tetrahydrofuran, dimethoxyethane (DME), ethyl acetate, isopropyl acetate, toluene, iso-octane, cyclohexane or water or mixtures thereof, optionally at elevated temperature.

Alternatively, according to a further process (process B), a compound of Formula (V) wherein A is furan or thiophene; $R^5$ is $-CO_2H$ or $-CO_2R^8$ and $R^6$ and $R^7$ independently represent hydrogen, $C_{1-6}$alkyl, $-CO_2H$, $-CO_2R^8$, cyano, tetrazol-5-yl, trifluoromethyl or $C_{1-6}$alkoxy, or when $R^6$ and $R^7$ are bonded to adjacent carbon atoms, $R^6$ and $R^7$ may, together with the carbon atoms to which they are bonded, form a fused 5- or 6-membered ring optionally containing one or two nitrogen, oxygen or sulfur atoms; may be prepared from the reaction of a compound of Formula (VIIa) where Y is bromine, iodine or triflate, with a compound of Formula (VIIb), in the presence of a suitable palladium catalyst and a suitable base, followed by reduction of the nitro group under standard conditions. Suitable palladium catalysts include, but are not limited to Pd(PPh$_3$)$_4$ (tetrakis(triphenylphosphine) palladium (0)). Suitable bases include, but are not limited to KOAc. Preferably, a solvent selected from toluene, DMA, DMF, NMP, isobutyronitrile and 1,2-diethoxy-ethane is present. A preferred solvent is toluene. The process is suitably carried out at elevated temperature, preferably at 80-120° C., more preferably at about 110° C. In process B, preferably R$^5$ is COOH or COOCH$_3$, preferably R$^6$ and R$^7$ represent hydrogen, and preferably Y represents bromine. More preferably, the compound of formula (V) is a 2-aryl-3-carboxy furan or thiophene or a 5-aryl-3-carboxy furan or thiophene.

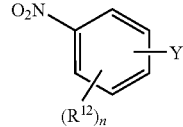

(VIIa)

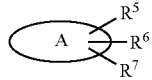

(VIIb)

For 2-aryl-3-carboxy furan or thiophene product, use of the palladium catalyst Pd(PPh$_3$)$_4$ in the presence of the base KOAc is preferred. On a preparative scale (50 g of Aryl bromide) the optimum conditions were found to be 1.4 eq of ethyl 3-furoate, 5 mol % Pd(PPh3)4, toluene reflux 24 hrs afforded the 2-aryl product in 76% yield. This represents an increased selectivity for synthesis over previously known processes. For 5-aryl-3-carboxy furan product, use of the palladium catalyst Pd/C in the presence of the solvent NMP and the base KOAc is preferred. For the 5-aryl-3-carboxy thiophene product use of the palladium catalyst Pd$_2$(dba)$_3$ in the presence of solvent NMP and the base KOAc is preferred.

Compounds of Formula (V) may also be prepared by reaction of a compound of Formula (VIII) with a compound of Formula (IX) using standard boronic acid coupling methods described above.

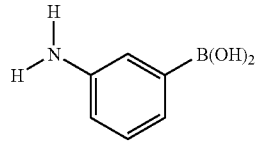

(IX)

Compounds of Formula (VI) may be prepared by reaction of a compound of Formula (X) with anhydrous HCl.

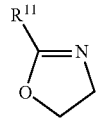

(X)

Further methods for preparing compounds of Formula (V) are disclosed in WO 97/21665.

Compounds of Formulae (VII), (VIIa), (VIIb), (VIII), (IX) and (X) are known compounds and can be prepared by processes well known in the art.

Those skilled in the art will appreciate that in the preparation of the compound of Formula (IA) or a solvate thereof it may be necessary and/or desirable to protect one or more sensitive groups in the molecule to prevent undesirable side reactions. The protecting groups used in the preparation of the compound of Formula (IA) may be used in a conventional manner. See for example Protective Groups in Organic Chemistry, Ed. J. F. W. McOmie, Plenum Press, London (1973) or Protective Groups in Organic Synthesis, Theodora Green, John Wiley and Sons, New York (1981). Conventional amino protecting groups may include for example aralkyl groups, such as benzyl, diphenylmethyl or triphenylmethyl groups; and acyl groups such as N-benzyloxycarbonyl or t-butoxycarbonyl. Conventional oxygen protecting groups may include for example alky silyl groups, such as trimethylsilyl or tert-butyldimethylsilyl; alkyl ethers such as tetrahydropyranyl or tert-butyl; or esters such as acetate.

Removal of any protecting groups present may be achieved by conventional procedures. An arylalkyl group such as benzyl, may be cleaved by hydrogenolysis in the presence of a catalyst, e.g., palladium on charcoal; an acyl group such as N-benzyloxycarbonyl may be removed by hydrolysis with, for example, hydrogen bromide in acetic acid or by reduction, for example by catalytic hydrogenation.

As will be appreciated, in any of the general processes described above it may be desirable or even necessary to protect any sensitive groups in the molecule as just described. Thus, a reaction step involving deprotection of a protected derivative of general Formula (IA) or a salt thereof may be carried out subsequent to any of the above described processes.

Thus, according to a further aspect of the invention, the following reactions may, if necessary and/or desired be carried out in any appropriate sequence subsequent to any of the general processes:

(i) removal of any protecting groups; and
(ii) conversion of a compound of Formula (IA) or a solvate thereof into a pharmaceutically acceptable solvate thereof.

EXAMPLES

The invention is further illustrated by the following intermediates and examples. All temperatures are in degrees centigrade.

Example 1
Preparation of 3'-[(2-{[(2R)-2-(3-chlorophenyl)-2-hydroxyethyl]amino}ethyl)amino][1,1'-biphenyl]-3-carboxylic acid hydrochloride
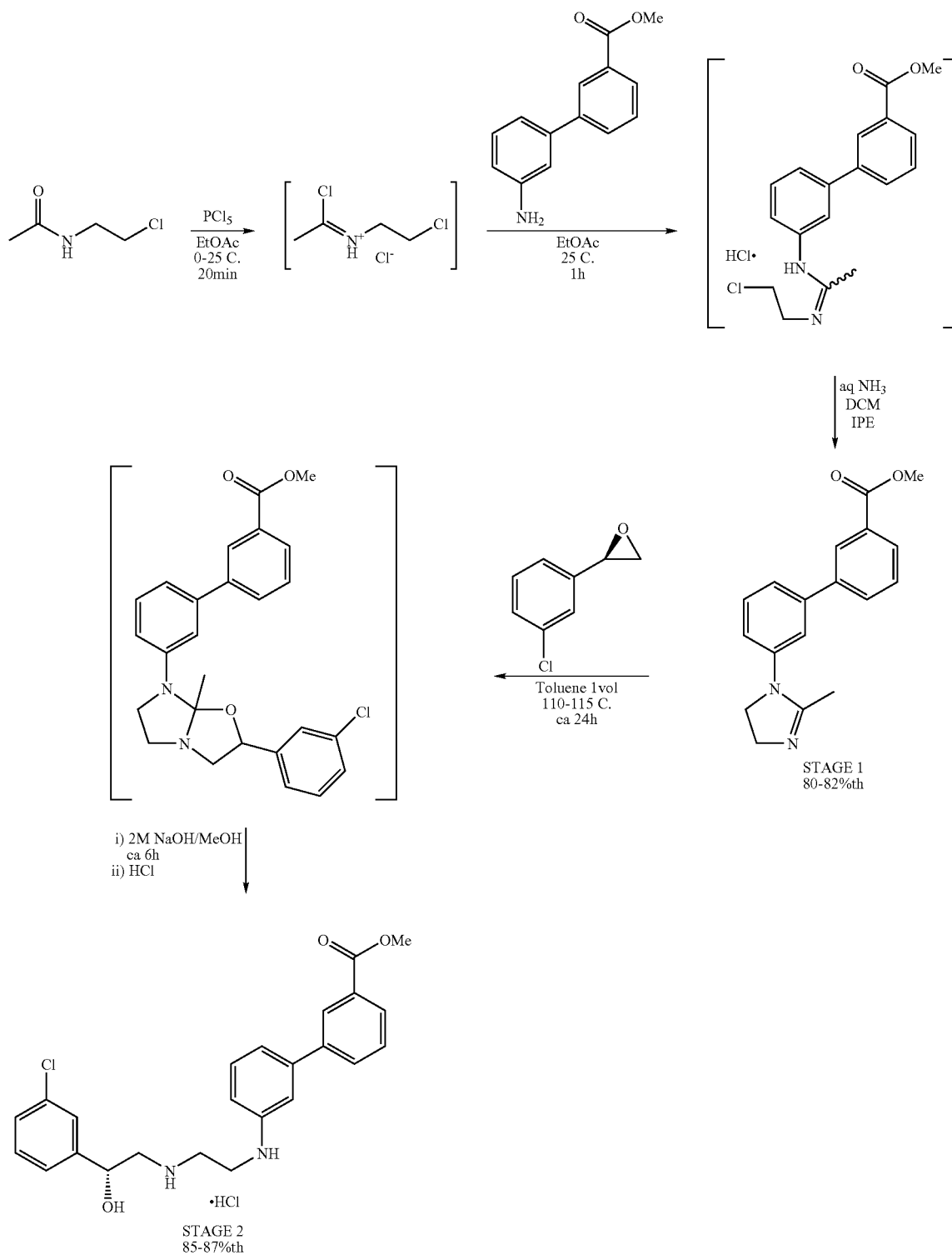
STAGE 1
80-82%th
STAGE 2
85-87%th

Stage 1 Preparation of methyl 3'-(2-methyl-4,5-dihydro-1H-imidazol-1-yl)-1,1'-biphenyl-3-carboxylate N-(2-chloroethyl)acetamide (0.64 wt) was added over ca. 20 min. to a stirred suspension of phosphorus pentachloride (1.1 wt) in ethyl acetate (2.2 vol.) at 0-5° C. under nitrogen. After stirring for ca. 20 min. at 0-5° C., a solution of Methyl 3'-amino(1,1'-biphenyl)-3-carboxylate (1 wt) in ethyl acetate (6.6 vol.) was added over ca. 30 min. at 0-5° C. Ethyl acetate (2 vol.) was then added and the mixture allowed to warm to 20-25° C., at which temperature it was stirred for at least 2 h then sampled for analysis. The mixture was cooled to 2-5° C. and aged for at least 1 h to allow complete precipitation of the product. The mixture was filtered and the solid washed with ethyl acetate (2×2 vol.). The colourless solid was sucked dry and sampled for analysis.

The amidine hydrochloride damp cake above was slurried in a mixture of dichloromethane (7.3 vol.) and water (ca. 7.3 vol.) at 20-25° C. Ammonium hydroxide solution (35% w/w ammonia, 0.77 wt.) was added and stirring continued for at least 1 h. The layers were allowed to separate, the bottom organic layer was filtered into another vessel via a cartridge line filter. Dichloromethane (3 vol.) was added as a line wash, and the solution concentrated at reduced pressure to ca. 3 vol. The solution was diluted with dichloromethane (5.8 vol.) and vacuum distillation recommenced, concentrating down to ca. 3 vol. The solution was diluted with dichloromethane (5.8 vol.) and vacuum distillation recommenced, concentrating down to ca. 3 vol. Diisopropyl ether (1.8 vol.) was added, followed by methyl 3'-(2-methyl-4,5-dihydro-1H-imidazol-1-yl)-1,1'-biphenyl-3-carboxylate seed crystals and the solution cooled to 2-5° C. to initiate crystallisation. Diisopropyl ether (7.0 vol.) was added and vacuum distillation recommenced, concentrating the solution to ca. 4.5 vol. Diisopropyl ether (4.4 vol.) was added, the slurry cooled to <5° C., and aged for at least 1 h. The product was collected by vacuum filtration, washed with diisopropyl ether (2×3 vol.) and dried in-vacuo at <50° C.

Expected yield: 80-82% theory.

$^1$H nmr (CDCl$_3$): 2.10 (s, 3H); 3.80-3.90 (m, 4H); 3.95 (s, 3H); 7.10 (d, 1H); 7.30 (s, 1H); 7.35-7.45 (m, 2H); 7.50 (t, 1H); 7.75 (d, 1H); 8.05 (d, 1H); 8.30 (s, 1H).

Stage 2 Preparation of 3'-[(2-{[(2R)-2-(3-chlorophenyl)-2-hydroxyethyl]amino}ethyl)amino][1,1'-biphenyl]-3-carboxylic acid hydrochloride Methyl 3'-(2-methyl-4,5-dihydro-1H-imidazol-1-yl)-1,1'-biphenyl-3-carboxylate (1 wt), (R)-3-chlorostyrene oxide (0.44 vol) and toluene (1 vol) were heated together at reflux for ca. 16-24 h. The reaction mixture was sampled for analysis by LC (complete when residual methyl 3'-(2-methyl-4,5-dihydro-1H-imidazol-1-yl)-1,1'-biphenyl-3-carboxylate <3% a/a @220 nm). The mixture was cooled to ca. 90° C. and 2M sodium hydroxide solution (5.3 vol.) followed by methanol (6.2 vol.) were added. The mixture was configured for distillation and ca. 3 vol. were removed at atmospheric pressure to give a homogeneous yellow solution (ca. 1 h). This was refluxed for ca. 5 h, sampled and checked by LC (<2% a/a N-acyl @242 nm). The solution was cooled to <50° C. and further methanol (4 vol.) was added.

Concentrated hydrochloric acid (1.5 vol.), methanol (3 vol.) and water (1 vol.) were heated to ca. 40-45° C. The hydrolysate mixture above was added over 30-40 min. to the acid solution. The resultant slurry was aged at 40-45° C. for at least 20 min. then cooled to 20-25° C. The product was collected by filtration, washed with water (2×2 vol.) then dried in vacuo at 60° C.

Expected yield 85-87% th $^1$H nmr (d$^6$-DMSO): 3.0-3.3 (m, 4H); 3.5-3.6 (m, 2H); 5.05 (d, 1H); 6.1 (bs, 1H); 6.35 (bs, 1H); 6.7 (d, 1H); 6.9-7.0 (m, 2H); 7.25 (t, 1H); 7.35-7.45 (m, 3H); 7.5 (s, 1H); 7.6 (t, 1H); 7.9 (d, 1H); 7.95 (d, 1H); 8.15 (s, 1H); 9.0 (bs, 1H); 9.5 (bs, 1H); 13.1 (bs, 1H).

Example 2

Preparation of 3-{3-[(2-{[(2R)-2-(3-chlorophenyl)-2-hydroxyethyl]amino}ethyl)amino]phenyl}isonicotinic acid

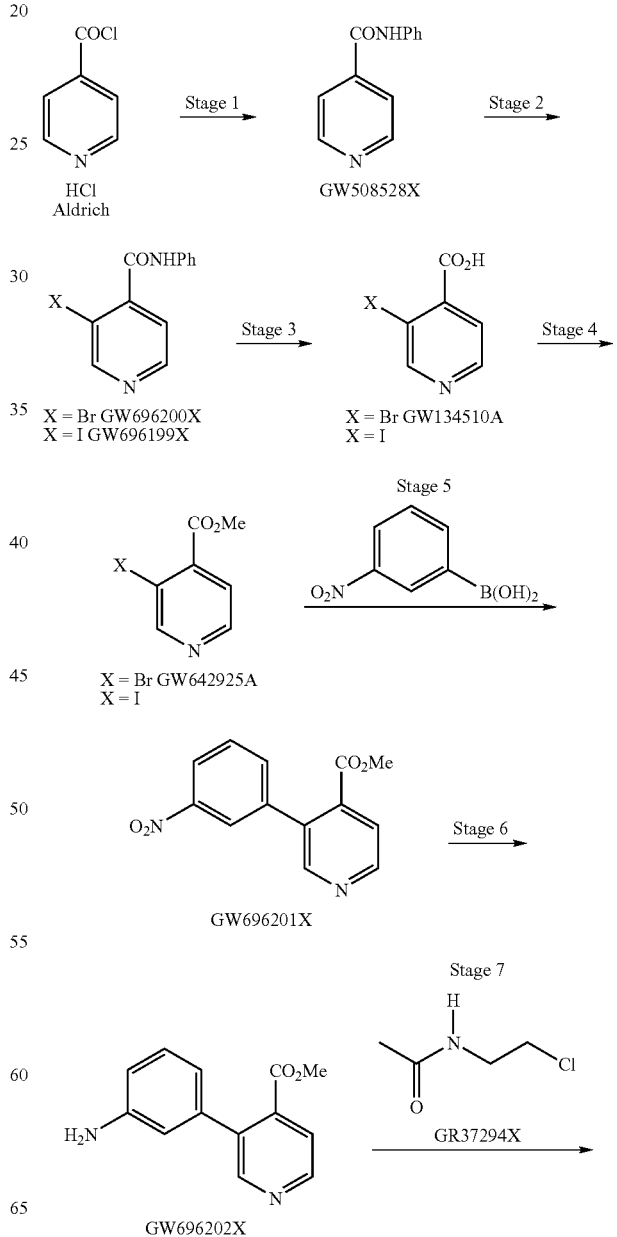

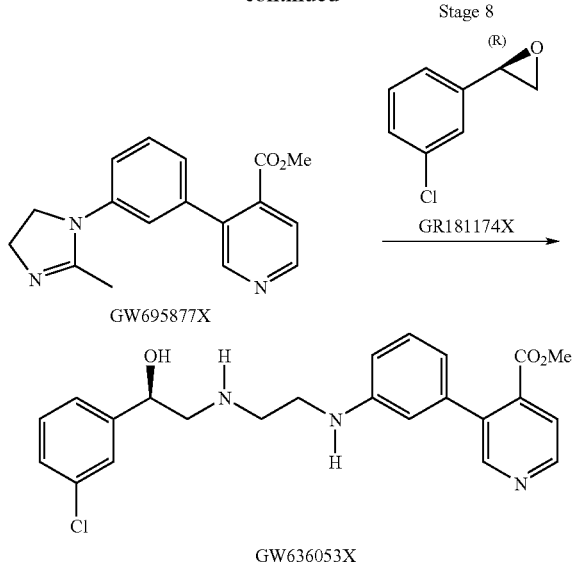

Stage 1 Preparation of N-Phenylisonicotinamide

Into a 4-necked RBF equipped with an overhead stirrer, J-Kem internal temperature probe, a reflux condenser and an addition funnel was placed isonicotinoyl chloride-hydrochloride (50 g, 0.28 mol). To this solid was added 500 ml of 1,2-dichloroethane and the slurry cooled to 0° C. using an ice/water bath. To the addition funnel was added a mixture of the aniline (31.4 g, 0.34 mol) and $Et_3N$ (59.5 g, 0.59 mol) in 50 ml of 1,2-dichloroethane. This mixture was slowly added to the slurry over 25 min. A slight exotherm was observed from 2.4° C. to 15° C. after the addition of the first 10 ml. The reaction mixture was observed to cool down slowly. The reaction mixture turned yellow and became heterogeneous. After 30 min., the ice bath was removed and the reaction heated to reflux for 1.5 h. Deionized water, 100 ml, was added and an off-white precipitate formed. The precipitate was collected by filtering through paper on a Buchner funnel and placed in a drying oven (60° C.) overnight to give 45 g (81% th) of an off-white crystalline solid.

$^1$H NMR (300 MHz, $d_6$-DMSO) δ: 10.48 (br s, 1H), 8.79 (d, 2H), 7.85 (d, 2H), 7.77 (d, 2H), 7.37 (t, 2H), 7.14 (t, 1H).

Stage 2(a) Preparation of N-Phenyl-3-bromoisonicotinamide

As described in Synthetic Communications 1997, 27, 1075-1086, a 4-necked RBF equipped with an overhead stirrer and a J-Kem internal temperature probe was placed N-phenylisonicotinamide (35.7 g, 0.18 mol) and anhydrous THF (700 ml). All material appeared to go into solution. This mixture was cooled to −69° C. in a dry ice/IPA bath. To this was slowly added nBuLi (158 ml of a 2.5 M solution in Hexanes) in three portions. While adding the first equivalent of nBuLi, an exotherm was observed raising the temperature to ca. −41° C. The orange reaction mixture was slightly heterogeneous. This was allowed to slowly warm to −5 to 0° C. over 1.5 hrs in a ice/brine bath. The reaction mixture was recooled to −72° C. and 1,2-dibromoethane (36 g, 0.189 mol) in 15 ml of THF was added. A slight exotherm was observed rising to −62° C. The reaction mixture was allowed to stir overnight. The reaction mixture was poured into a flask containing 10 vol. $SiO_2$. Methanol (100 ml) was added and the mixture was concentrated under reduced pressure. The dried silica gel was then placed on top of a bed of silica gel. The plug of silica gel was washed with 40% ethyl acetate/Hexane as eluent. Concentration of 10 liters of solvent afforded an off-white solid. The material was placed in vacuum drying at 60° C. overnight to provide 34 g (68% th) of an off-white solid.

$^1$H NMR (300 MHz, $d_6$-DMSO) δ: 10.65 (s, 1H), 8.87 (s, 1H), 8.68 (d, 1H), 7.65 (m, 3H), 7.37 (t, 2H), 7.14 (t, 1H).

Stage 2(b) Preparation of N-Phenyl-3-iodoisonicotinamide

Into a 4-necked RBF equipped with an overhead stirrer and a J-Kem internal temperature probe was placed N-phenylisonicotinamide (35.1 g, 0.18 mol) and anhydrous THF (700 ml). All material appeared to go into solution. This mixture was cooled to −69° C. in a dry ice/IPA bath. To this was slowly added nBuLi (156 ml of a 2.5 M in Hexanes) in two portions. While adding the first equivalent of nBuLi, an exotherm was observed raising the temperature to approx. −41° C. The orange reaction mixture was slightly heterogeneous. This was allowed to slowly warm to 12° C. over 2 h. This mixture was re-cooled to −70° C. At this point, a THF solution (175 ml) of iodine (47.2 g, 0.19 mol) was added. This was allowed to warm and stirred at room temperature for 14 h. To this solution was added 150 ml of a saturated solution of potassium meta-bisulfite and diluted with $CH_2Cl_2$. The two layers were separated and the organic layer was extracted with brine. The two layers were separated and the organic layer was dried over $MgSO_4$, filtered and concentrated under reduced pressure to give a black oil. This material was purified by $SiO_2$ column chromatography using 40% ethyl acetate/Hexane as eluent. Concentration gave 38.6 g (67% th) of an off-white solid.

Stage 3 Preparation of 3-Bromoisonicotinic acid hydrochloride

To an RBF equipped with a condenser and outfitted with a heating mantle was placed the N-phenyl-3-bromo-isonicotinamide (34 g, 0.123 mol) and 200 ml of 25% HCl. The reaction was left to stir for 3 days. The mixture was cooled to room temperature, and diluted with ethyl acetate. The aqueous layer was extracted and the two layers separated. To the aqueous layer, solid $Na_2CO_3$ was added until the pH~4-5 and a dark oil layer appeared. This was then diluted and extracted with ethyl acetate. The two layers were separated and the aqueous layer was concentrated under reduced pressure to give an off-white solid. To this 100 ml of 2M HCl was added and the solids collected. The off-white solids were placed in a vacuum oven at 60° C. overnight. Yield: 22.4 g (76% th).

$^1$H NMR (300 MHz, $d_6$-DMSO) δ: 8.83 (s, 1H), 8.61 (d, 1H), 7.65 (d, 1H).

This method was also applied to the hydrolysis of 3-iodoisonicotinic acid.

Stage 4 Preparation of Methyl 3-bromoisonicotinate hydrochloride

To a stirred suspension of 3-bromoisonicotinic acid hydrochloride (27.4 g, 0.10 mol) in ethyl acetate (250 ml) was added one drop of DMF followed by thionyl chloride (18.5 g, 0.16 mol). The mixture was heated at reflux for 1 h and allowed to cool to room temperature. The mixture was then concentrated under reduced pressure to give an off-white solid. To this was added methanol and this was refluxed for 2 hrs. The mixture was then concentrated under reduced pressure and diluted with ethyl acetate. The precipitate was collected on filter paper on a Buchner funnel. The white solid was washed with ethyl acetate and air-dried. The white solid was placed in a vacuum oven at 60° C. overnight with a nitrogen bleed. Yield: 18.5 g (71% th).

$^1$H NMR (300 MHz, $d_6$-DMSO) δ: 8.80 (s, 1H), 8.59 (d, 1H), 7.62 (d, 1H), 3.91 (s, 3H).

This method was also applied to the esterification of 3-iodo-isonicotinic acid.

Stage 5 Preparation of Methyl 3-(3-Nitrophenyl)Isonicotinate

To an RBF equipped with a heating mantle and reflux condenser was placed the methyl 3-iodoiso nicotinate (5.1 g, 0.02 mmol), a 4:1 mixture of toluene/ethanol (75 ml), 1.0N solution of sodium carbonate (25 ml) followed by dichloro [1,1'-bis(diphenylphosphino)-ferrocene]palladium(II) dichloromethane adduct (1.4 g, 0.002 mol). This reaction mixture was heated to reflux for 6 h. The purple reaction mixture was filtered through a compressed pad of Celite, which was washed with ethyl acetate. The ethyl acetate layer was washed first with deionized water and then washed 3× with 10% aqueous HCl. The aqueous layers were concentrated in half under reduced pressure and then diluted with ethyl acetate. The aqueous layer was neutralized with solid sodium carbonate, extracted and separated. The organic layer was dried over MgSO$_4$, filtered and concentrated under reduced pressure to give 1.9 g (43% th) of an off-white solid.

$^1$H NMR (300 MHz, $d_6$-DMSO) δ: 8.81 (d, 1H), 8.78 (s, 1H), 8.30 (d, 1H), 8.23 (s, 1H), 7.87-7.74 (m, 3H), 3.37 (s, 3H).

Stage 6 Preparation of Methyl 3-(3-aminophenyl)isonicotinate

Into an RBF was placed methyl 3-(3-nitrophenyl)isonicotinate (1.85 g, 7.16 mmol) and to this was added methanol (50 ml), ammonium formate (6.0 g, 35.8 mmol) and 5 wt % Pd/C (Degussa type). No initial exotherm was noticed (to the touch) and no bubbling or gas evolution was observed. After 2 h, some SM was observed to be undissolved and THF (25 ml) was added to aid in solubility. The reaction was slow at room temperature. The reaction mixture was then placed on the Buchi hydrogenator overnight. The mixture was then filtered through a pad of Celite and washed with ethyl acetate. This solution was washed with water, separated and the organic layer was dried over MgSO$_4$, filtered and concentrated under reduced pressure. The orange oil was purified by silica gel flash chromatography using 30% ethyl acetate/Hexanes as eluent to yield 1.15 g (71% th) of an orange oil.

$^1$H NMR (300 MHz, $d_6$-DMSO) δ: 8.67 (, d, 1H), 8.63 (s, 1H), 7.59 (d, 1H), 7.08 (t, 1H), 6.61-6.44 (m, 3H), 5.24 (br s, 2H), 3.67 (s, 3H).

Stage 7 Preparation of methyl 3-[3-(2-methyl-4,5-dihydro-1H-imidazol-1-yl)phenyl]isonicotinate N-(2-chloroethyl)acetamide (0.32 g) in ethyl acetate (5 ml) was added over 10 min. to a stirred suspension of phosphorus pentachloride (0.55 g) in ethyl acetate (2 ml) at 0° C. under nitrogen to give a clear pale straw solution. After 45 min. at 0° C. a solution of methyl 3-(3-aminophenyl)isonicotinate (0.4 g) in dichloromethane (10 ml) was added over 15 min. at 0-5° C. The mixture was stirred at 0° C. for 10 min. and then allowed to warm up to 20° C. After 3 h the mixture was treated with ammonium hydroxide solution (28%, 5 ml) over 10 min. and stirring continued for ca. 1 h. The layers were allowed to separate, the organic layer was collected, dried over anhydrous magnesium sulfate, and concentrated under reduced pressure. The residue was purified by silica gel chromatography (dichloromethane:methanol:ammonia=100:10:1, v/v/v) to give 0.25 g (48%) of yellow oil.

$^1$H NMR (400, CDCl$_3$) δ: 8.70 (d, 1H), 8.65 (s, 1H), 7.62 (d, 1H), 7.39 (t, 1H), 7.11-7.00 (m, 3H), 3.87-3.80 (m, 2H), 3.71 (s, 3H), 3.60-3.56 (m, 2H), 2.08 (s, 3H).

Stage 8 Preparation of 3-{3-[(2-{[(2R)-2-(3-chlorophenyl)-2-hydroxyethyl]amino}ethyl)amino]phenyl}isonicotinic acid A solution of methyl 3-[3-(2-methyl-4,5-dihydro-1H-imidazol-1-yl)phenyl]isonicotinate (0.25 g) and (R)-3-chlorostyrene oxide (0.13 g) in anhydrous toluene (2 ml) was heated at reflux (ca. 110° C.) for 18 h. The mixture was cooled to ca. 50° C., 1M sodium hydroxide solution (4.8 ml) and methanol (3 ml) were added over 5-10 min. The apparatus was configured to distill out 4 ml of solvents under atmospheric pressure. The homogeneous mixture obtained was heated at reflux for 2 h. The mixture was cooled to <50° C., and concentrated hydrochloric acid (36%, 0.3 ml) was added dropwise to adjust pH to 7. The aqueous solution was loaded on to silica gel column and eluted with a mixture of dichloromethane and methanol (8/2, v/v). The product was isolated as 0.2 g (57%) of hygroscopic brown solid.

$^1$H NMR (400, CD$_3$OD) δ: 8.48 (s, 1H), 8.45 (d, 1H), 7.44-7.40 (m, 2H), 7.33-7.27 (m, 3H), 7.16 (t, 1H), 6.86-6.80 (m, 2H), 6.66 (d, 1H), 5.01-4.98 (m, 1H), 3.49-3.45 (m, 2H), 3.32-3.20 (m, 3H), 3.14-3.09 (m, 1H).

Example 3

Preparation of 2-{3-[(2-{[(2R)-2-(3-chlorophenyl)-2-hydroxyethyl]amino}ethyl)amino]phenyl}-3-furoic acid

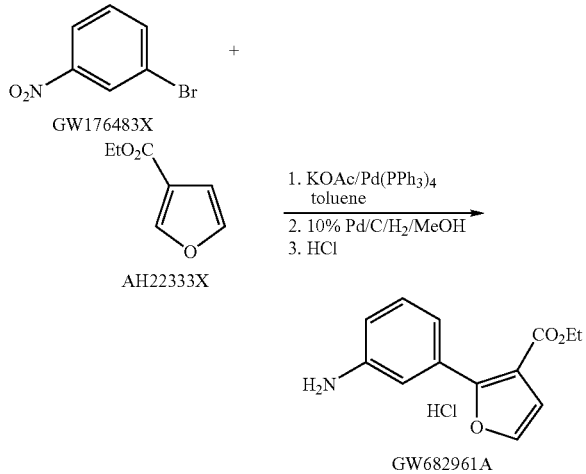

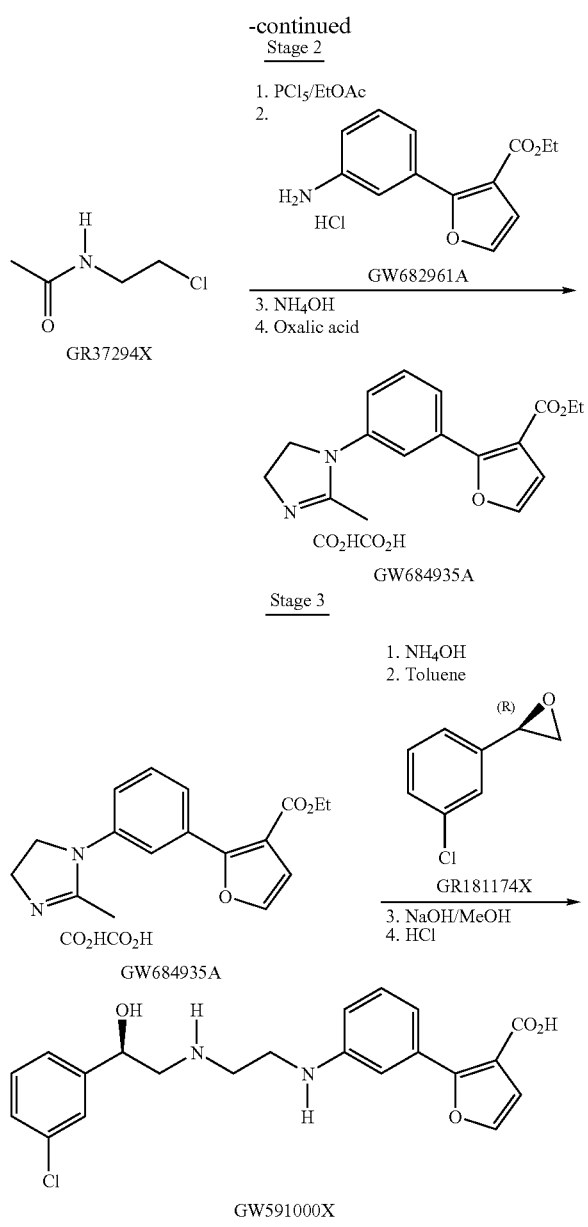

Stage 1 Preparation of ethyl 2-(3-aminophenyl)-3-furoate hydrochloride

To a stirred solution of 1-bromo-3-nitrobenzene (50 g) and ethyl 3-furoate (48.6 g) in toluene (500 ml) were added potassium acetate (36.4 g) and tetrakis(triphenylphosphine)palladium(0) (14.3 g). The mixture was heated at reflux for 66 h, cooled to room temperature, and filtered through Celite (50 g). The filtercake was rinsed with ethyl acetate (2×200 ml). The combined filtrate/rinse was concentrated to an oil. Methanol (500 ml) and 10% palladium on carbon (50% wet paste, 3.2 g) were added. The mixture was stirred under an atmosphere of hydrogen until uptake ceased. The mixture was filtered through Celite (50 g), and the filtercake was rinsed with ethyl acetate (200 ml). The combined filtrate/rinse was concentrated to an oil, and ethyl acetate (250 ml) was added. The solution was washed with water (100 ml). The organic phase was dried over sodium sulfate, filtered, and concentrated to an oil. Dichloromethane (50 ml) was added, and the resulting solution was filtered through a silica gel plug (100 g). The plug was rinsed with dichloromethane (2500 ml) to extract all ethyl 2-(3-aminophenyl)-3-furoate hydrochloride. The combined filtrate/rinse was concentrated to an oil, and methyl tert-butyl ether (250 ml) was added. To this stirred solution was slowly added 4.0 M HCl in dioxane (93 ml). After aging for 15 minutes at 0-5° C., the precipitate was collected by filtration, washed with methyl tert-butyl ether (2×100 ml), and dried in vacuo at 45-50° C. to yield 46.8 g (71% th) of the title compound as a beige solid.

$^1$H NMR (300 MHz, d$_6$-DMSO) δ; 7.90 (d, 1H), 7.78 (m, 2H), 7.51 (t, 1H), 7.30 (d, 1H), 4.25 (q, 2H), 1.26 (t, 3H).

Stage 2 Preparation of ethyl 2-[3-(2-methyl-4,5-dihydro-1H-imidazol-1-yl)phenyl]-3-furoate N-(2-chloroethyl)acetamide (1.21 g) in ethyl acetate (10 mL) was added over 10 min to a stirred suspension of phosphorus pentachloride (2.08 g) in ethyl acetate (2 ml) at 0° C. under nitrogen to give a clear pale straw solution. After 45 min. at 0° C. toluene (12 ml) was added, and ethyl 2-(3-aminophenyl)-3-furoate hydrochloride (1.78 g) was added in one portion into the above solution at 0-5° C. The mixture was stirred at 0-5° C. for 10 min. and then allowed to warm up to 20° C. After 2 h formation of the amidine was essentially complete (HPLC ethyl 2-(3-aminophenyl)-3-furoate hydrochloride <2% @220 nm, a/a). The mixture was cooled to 0-5° C., crushed ice (18 g) was added over 20 min. to destroy phosphorus oxychloride. Ammonium hydroxide (28%, 6.49 mL) was added at a rate that the internal temperature was kept below 25° C. (ca. 15 min). After 1 h at 20° C. additional ethyl acetate (12 ml) added to the above mixture, the organic layer was separated, washed with deionized water (2×12 ml), and concentrated under reduced pressure. The residue was dissolved in acetone (5 ml) and ethyl acetate (5 ml), and treated with oxalic acid (0.72 g) at 40° C. for 30 min. After aging at <20° C. for at least 12 h, the precipitate was collected by filtration, washed with acetone (2×0.5 vol), and dried in vacuo at 45-50° C. to yield 1.9 g (73%) of white solid.

$^1$H NMR (400, d$_6$-DMSO) δ: 8.00 (s, 1H), 7.92-7.90 (m, 2H), 7.64-7.55 (m, 2H), 6.90 (d, 1H), 4.32 (t, 2H), 4.22 (q, 2H), 3.93 (t, 2H), 2.22 (s, 3H), 1.24 (t, 3H).

Stage 3 Preparation of 2-{3-[(2-{[(2R)-2-(3-chlorophenyl)-2-hydroxyethyl]amino}ethyl)amino]phenyl}-3-furoic acid Ammonium hydroxide (28%, 13 ml) was added over 10 min. to a mixture of ethyl 2-[3-(2-methyl-4,5-dihydro-1H-imidazol-1-yl)phenyl]-3-furoate (13.0 g), deionized water (104 ml), and toluene (104 ml). After 30 min stirring, the organic layer was collected, washed with deionized water (26 ml), and concentrated to ca. 30 ml to remove traces of water azetropically. (R)-3-Chlorostyrene oxide (5.17 g) was added, and the resultant was heated under nitrogen at 110° C. for at least 14 h. The mixture was cooled to ca. 50° C. 1M Sodium hydroxide aqueous solution (77.8 ml) and methanol (39 ml) were added, and the apparatus was configured for distillation. After ca. 1 h, the homogeneous solution obtained was heated at reflux (ca. 4 h) until the hydrolysis was complete (HPLC acetate <2% @220 nm, a/a). The mixture was cooled to <50° C. Methanol (26 ml) and 1M hydrochloric acid (78 ml) were heated to ca. 50° C. The reaction mixture from above was added over 20 min, and the resultant slurry was cooled to <20° C. and aged for a further 30 min. The product was collected by filtration, washed with deionized water (2×26 ml), and dried in vacuo at 50° C. to yield 12.7 g (95%) of off-white solid.

$^1$H NMR (400, d$_6$-DMSO) δ: 7.66 (d, 1H), 7.39 (s, 1H), 7.32-7.26 (m, 4H), 7.12-7.04 (m, 2H), 6.72 (d, 1H), 6.58 (d, 1H), 5.75 (br, 1H), 4.78-4.74 (dd, 1H), 3.17 (t, 2H), 2.92-2.70 (m, 4H).

The invention claimed is:

1. A compound of Formula (IV):

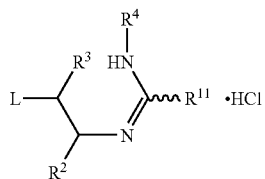

(IV)

or a salt thereof wherein:
R$^2$ represents hydrogen or C$_{1-6}$alkyl;
R$^3$ represents hydrogen or C$_{1-6}$alkyl;
L represents halogen;
R$^4$ represents a group (W):

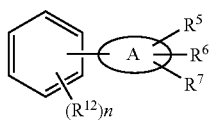

(W)

wherein A represents an aryl; R$^5$ represents cyano or —CO$_2$R$^8$; R$^6$ and R$^7$ independently represent hydrogen, C$_{1-6}$alkyl, —CO$_2$R$^8$, cyano, halogen, trifluoromethyl or C$_{1-6}$alkoxy; each R$^{12}$ independently represents substituents selected from: C$_{1-6}$alkyl, halogen, trifluoromethyl and C$_{1-6}$alkoxy, and n represents an integer from 0-4;
R$^8$ and R$^9$ independently represent C$_{1-6}$alkyl; and
R$^{11}$ represents C$_{1-6}$alkyl or aryl optionally substituted by C$_{1-6}$alkyl or halogen.

2. The compound of Formula (IV) according to claim 1 wherein
R$^2$ is hydrogen;
R$^3$ is hydrogen;
R$^4$ is W
R$^5$ is —CO$_2$R$^8$;
R$^6$ and R$^7$ are both hydrogen;
R$^{11}$ represents methyl; and
n is 0.

3. The compound according to claim 1, wherein said compound has the formula:

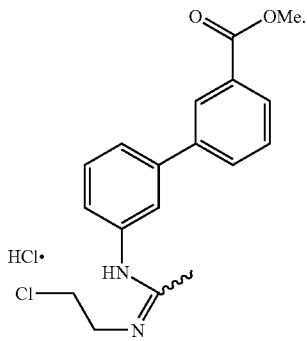

* * * * *